US005804393A

United States Patent [19]
Geiser et al.

[11] Patent Number: 5,804,393
[45] Date of Patent: Sep. 8, 1998

[54] **ANTIBODIES DIRECTED TO THE BINDING PROTEINS OF *BACILLUS THURINGIENSIS* AND THEIR USE**

[75] Inventors: Martin Geiser, Ettingen; Pascale Oddou Stock, Basel, both of Switzerland; Herbert Hartman, Isernhagen, Germany

[73] Assignee: Thermo Trilogy Corporation, Columbia, Md.

[21] Appl. No.: 922,254

[22] Filed: Sep. 2, 1997

Related U.S. Application Data

[63] Continuation of Ser. No. 754,334, Nov. 22, 1996, abandoned, which is a continuation of Ser. No. 317,000, Oct. 3, 1994, abandoned, which is a continuation of Ser. No. 918,543, Jul. 21, 1992, abandoned.

[30] Foreign Application Priority Data

| Jul. 25, 1991 | [CH] | Switzerland | 2231/91 |
| Aug. 25, 1991 | [CH] | Switzerland | 2517/91 |

[51] Int. Cl.$^6$ .................................................. G01N 33/53
[52] U.S. Cl. .................. 435/7.2; 435/7.32; 435/7.92; 435/7.93; 435/975; 436/501; 436/503; 436/547; 436/548; 436/808; 530/387.1; 530/387.2; 530/388.22; 530/389.1
[58] Field of Search .................................... 435/7.2, 7.32, 435/7.92, 7.93, 975; 436/501, 503, 547, 548, 808; 530/387.1, 388.22, 388.4, 389.1, 389.15, 387.2

[56] References Cited

FOREIGN PATENT DOCUMENTS

| 0 292 435 | 11/1988 | European Pat. Off. . |
| 0 317 511 | 5/1989 | European Pat. Off. . |
| 0 342 633 | 11/1989 | European Pat. Off. . |
| 0 400 246 | 12/1990 | European Pat. Off. . |

OTHER PUBLICATIONS

Bradford, M.M., "A Rapid and Sensitive Method for the Quantitation of Microgram Quantities of Protein Utilizing the Principle of Protein–Dye Binding", *Anal. Biochem.*, 72:248–254 (1976).

Caramori, T. et al., "In vivo Generation of Hybrids Between Two *Bacillus thuringiensis* Insect–toxin–encoding Genes", *Gene*, 98:37–44 (1991).

Delafield, F.P. et al., "Immunological Homology Between Crystal and Spore Protein of *Bacillus thuringiensis*", *J. Bacteriol.*, 96(3):713–720 (1968).

Dixon, B., "B.T. Toxins Studied", *Biotechnology*, 9:415 (1991).

Garczynski, S.F., et al., "Identification of Putative Insect Brush Border Membrane–Binding Molecules Specific to *Bacillus thuringiensis* δ–Endotoxin by Protein Blot Analysis", *Applied and Environ. Microbiol.*, 57(10):2816–2820 (1991).

Ge., A.Z., et al., "Location of the *Bombyx mori* Specificity Domain on a *Bacillus thuringiensis* δ–endotoxin Protein", *PNAS*, 86:4037–4041 (1989).

Geiser, M., et al., "The Hypervariable Region in the Genes Coding for Entomopathogenic Crystal Proteins of *Bacillus thuringiensis*: Nucleotide Sequence of the kurhdl Gene of subsp. kurstaki HD1", *Gene*, 48:109–118 (1986).

Haider, M.Z., et al., "Analysis of the Molecular Basis of Insecticidal Specificity of *Bacillus thuringiensis* Crystal δ–endotoxin", *Biochem J.*, 248:197–201 (1987).

Harlow, E. et al., *Antibodies, A Laboratory Manual*, pp. 59–67, (Cold Spring Harbor Laboratory, 1988).

Hofte, H. et al., "Insecticidal Crystal Proteins of *Bacillus thuringiensis*", *Microbiological Reviews*, 53(2):242–255 (1989).

Huber–Lukac, M. et al., "Characterization of Monoclonal Antibodies to a Crystal Protein of *Bacillus thuringiensis* subsp. kurstaki", *Infection and Immunity*, 54(1):228–232 (1986).

Knowles, B.H. et al., "Characterization and Partial Purification of a Plasma Membrane Receptor for *Bacillus thuringiensis var kurstaki* Lepidopteran–specific δ–endotoxin", *J. Cell Sci.*, 83:89–101 (1986).

Laemmli, J.K., "Cleavage of Structural Proteins during the Assembly of the Head of Bacteriophage T4", *Nature*, 227:680–685 (1970).

Madara, P.J., et al., "Affinity Purification of Polyclonal Antibodies from Antigen Immobilized in Situ in Sodium Dedecyl Sulfate–Polyacrylamide Gels", *Anal. Biochem.*, 187:246–250 (1990).

Oddou, P., et al., "Identification and Characterization of *Heliothis virescens* Midgut Membrane Proteins Binding *Bacillus thuringiensis* δ–endotoxin", *Eur. J. Biochem.*, 202:673–680 (1991).

(List continued on next page.)

*Primary Examiner*—Jeffrey Stucker
*Attorney, Agent, or Firm*—Valerie E. Looper

[57] ABSTRACT

The present invention relates to an antibody which reacts specifically with the binding proteins for *Bacillus thuringiensis* δ-endotoxins and their derivatives. The invention further relates to an anti-idiotype antibody which reacts specifically with the binding proteins for *Bacillus thuringiensis* δ-endotoxins and their derivatives. The invention also provides a test kit which contains a novel antibody. The invention further relates to a method of isolating a novel *B. thuringiensis* δ-endotoxin, to said novel *B. thuringiensis* δ-endotoxin, to a method of identifying a novel *B. thuringiensis* δ-endotoxin which recognises a novel binding protein, to the novel *B. thuringiensis* δ-endotoxin, to a method of determining the amount of binding protein present, and to a method of reducing the resistance development potential in pest control. The invention further relates to the use of novel antibodies and test kits for analysing the immunological cross reactivity of toxin binding proteins to determine their degree of relationship and to determine the availability and accessibility of a binding protein for the corresponding toxin in different insects. The invention also relates to the use of the novel antibodies for analysing resistance which is attributable to the lack of the binding protein or of the binding sites.

16 Claims, No Drawings

OTHER PUBLICATIONS

Schnepf, H.E., et al., "The Amino Acid Sequence of a Crystal Protein from *Bacillus thuringiensis* Deduced from the DNA Base Sequence", *J. Biol. Chem.*, 260(10):6264–6272 (1990).

Towbin, H., et al., "Electrophoretic Transfer of Proteins from Polyacrylamide Gels to Nitrocellulose Sheets: Procedure and Some Applications", *PNAS*, 76(9):4350–4354 (1979).

Van Rie., J., et al., "Specificity of *Bacillus thuringiensis* δ–endotoxins: Importance of Specific Receptors on the Brush Border Membrane of the Mid–gut of Target Insects", *Eur. J. Biochem.*, 186:239–247 (1989).

Van Rie, J., et al., "Mechanism of Insect Resistance to the Microbial Insecticide *Bacillus thuringiensis*", *Science*, 247:72–74 (1990).

Wolfersberger, M., et al., "Preparation and Partial Characterization of Amino Acid Transporting Brush Border Membrane Vesicles from the Larval Midgut of the Cabbage Butterfly (*pieris brassicae*)", *Comp. Biochem. Physiol.*, 86A(2):301–308 (1987).

ANTIBODIES DIRECTED TO THE BINDING PROTEINS OF *BACILLUS THURINGIENSIS* AND THEIR USE

This application is a continuation of application Ser. No. 08/754,334, filed Nov. 22, 1996, now abandoned, which is a continuation of application Ser. No. 08/317,000, filed Oct. 3, 1994, now abandoned, which is a continuation of application Ser. No. 07/918,543, filed Jul. 21, 1992, now abandoned.

The present invention relates to an antibody which reacts specifically with the binding proteins for *Bacillus thuringiensis* δ-endotoxins and their derivatives. The invention further relates to an anti-idiotype antibody which reacts specifically with the binding proteins for *Bacillus thuringiensis* δ-endotoxins and their derivatives. The invention also provides a test kit which contains a novel antibody. The invention further relates to a method of isolating a novel *B. thuringiensis* δ-endotoxin, to said novel *B. thuringiensis* δ-endotoxin, to a method of identifying a novel *B. thuringiensis* δ-endotoxin which recognises a novel binding protein, to the novel *B. thuringiensis* δ-endotoxin, to a method of determining the amount of binding protein present and to a method of reducing the resistence development potential in pest control. The invention further relates to the use of novel antibodies and test kits for analysing the immunological cross-reactivity of toxin binding proteins to determine their degree of relationship and to determine the availability and accessibility of a binding protein for the corresponding toxin in different insects. The invention also relates to the use of the novel antibodies for analysing resistance which is attributable to the lack of the binding protein or of the binding sites.

During sporulation, *B. thuringiensis* produces crystalline inclusion bodies containing proteins which are lethal to specific insect larvae. These proteins are known as δ-endotoxins or as insecticidal crystal proteins (ICPs). The different ICPs can be classified according to the scheme of Höfte and Whitely (1989). Known ICPs include CryIA(a), CryIA(b), CryIA(c) and CryIC toxins. The native crystal proteins are inactive protoxins which, after ingestion by the larvae, are dissolved in the alkaline insect gut and proteolytically activated. The activated toxins bind to one or more proteins on the brush border membrane (BBM) of the midgut epithelial cells of target insects and destroy the epithelial cells of the gut, resulting in the death of the larvae.

In biological pest control, *B. thuringiensis* toxins are used mainly in the form of spore suspensions. However, different plants have also been transformed with *B. thuringiensis* toxin genes in order to impart to them resistance to pests (q.v. EP 292 435, EP 317 511). In the course of time the pests develop a resistance to the toxins which is linked to the ability of toxin binding proteins to bind to the BBM (Dixon, 1991; van Rie et al., 1990). Certain determinants on the toxin determine the specificity of *B. thuringiensis* toxins. These determinants are localised in the variable regions of the C-terminal half of the activated toxin (Caramori et al., 1991; Ge et al., 1989; Schnepf et al., 1990).

If the binding protein for a specific toxin is lost, or if its recognition region is so altered that it no longer binds the specific toxin, then the insect loses its susceptibility to the particular toxin and becomes resistant. The use of different toxins which bind to different binding proteins makes it possible to forestall rapid development of resistance. Knowledge of the interplay of toxin and corresponding binding protein makes it possible to select and combine those toxins which occupy the different binding proteins in the BBM of the midgut epithelium of target insects (EP 400 246). *B. thuringiensis* and plants can be transformed with the corresponding genes of the toxins so combined. The probability that insects will be resistant to the recombinant *B. thuringiensis* or the transgenic plant is thereby significantly diminished, for it requires a number of simultaneous mutations to become resistant simultaneously to toxins which bind to different binding proteins (EP 400 246).

The interaction between toxin and binding protein can be investigated, inter alia, with the aid of immunological methods. Such methods have been used for analysis for some considerable time and comprise utilising the specific binding between antigen and antibody. The antigen, i.e. the compound to be analysed, is injected into a mammal, typically a rabbit, a mouse or a rat, repeatedly at an interval of several weeks. The immune system of the animal produces antibodies which bind specifically to the antigen and whose binding region constitutes a negative image of the binding region of the antigen.

The fusion of the antibody producing cells with, typically, myeloma cells results in the formation of so-called hybridoma cells, with the aid of which monoclonal antibodies can be produced. The methods employed are described in the literature and known to the person skilled in the art.

The present invention relates to an antibody which reacts specifically with the binding proteins for *B. thuringiensis* δ-endotoxins and their derivatives. A preferred embodiment of the invention relates to an antibody which reacts specifically with the binding proteins for the *B. thuringiensis* CryIA(b) δ-endotoxin and its derivatives, preferably an antibody which reacts specifically with the Heliothis binding protein for *B. thuringiensis* CryIA(b) δ-endotoxin and its derivatives, more particularly an antibody which reacts specifically with the *H. virescens* 170 kDa binding protein for the *B. thuringiensis* CryLA(b) δ-endotoxin and its derivatives.

Within the scope of this invention, derivatives of *B. thuringiensis* δ-endotoxins will be understood as meaning insecticidal derivatives of these toxins which are obtainable by modifications of a chemical or microbiological nature.

The novel antibody can be obtained by producing binding proteins for *B. thuringiensis* δ-endotoxins and their derivatives from BBM vesicles of the midgut of insects and used to produce the said antibody by known methods (q.v. Harlow and Lane, 1988). The procedure may typically comprise producing (a) binding proteins for *B. thuringiensis* δ-endotoxins and their derivatives from BBM vesicles of the midgut of insects, (b) immunising a mammal, for example a rabbit, a mouse or a rat, with the binding proteins, and (c1) selecting the immunoglobulins which are directed against the binding proteins for *B. thuringiensis* δ-endotoxins and their derivatives, or (c2) fusing spleen cells of the immunised animal with corresponding myeloma cells, selecting specific hybridoma cells and producing the desired antibodies using said hybridoma cells.

The preparation of BBM vesicles from the midgut of insects is known. The procedure may be as follows: fourth instar larvae are chilled on ice for 15 minutes. The midguts are then carefully removed from the larvae. Each midgut is opened with a longitudinal cut and then rinsed free of gut content with Hoyle's Ringer solution (140 mM NaCl: 9.4 mM KCl; 3.95 mM $MgCl_2 \cdot 6\ H_2O$; 3.6 mM $NaHCO_3$; 6.55 mM $Na_2HPO_4$; 5.44 mM $CaCl_2$, pH 7.2). After removal of the peritrophic membrane, the midguts are immediately frozen in 300 mM of mannitol; 5 mM EGTA; 17 mM tris-HCl pH 7.5 and stored at −70° C. until use.

BBM vesicles (BBMV) of *H. virescens, H. zea, Spodoptera littoralis, S. exigua* and *S. litura* are then prepared as described by Wolfersberger et al. (1987) using the following protease inhibitors: 1 µg/ml of leupeptin, 1 µg/ml of antipain, 5 µg/ml of aprotinin, 10 µg/ml of trypsin inhibitor from soya, 10 µg/ml of benzamidine hydrochloride, 1 µg/ml of pepstatin A, 1 mM of PMSF. The final pellet is resuspended in PBS or dissolved in a buffer containing 40 mM of tris-HCl pH 7.5, 10 mM of $MgCl_2$, 5 mM of EGTA, 30% of glycerol und 10 mM of CHAPS. The protein content of the BBMV is determined by the method of Bradford (1976) using BSA as standard SDS-PAGE is performed according to Laemmli (1970).

The CryLA(b) binding protein from *H. virescens* is typically obtained via a preparative SDS-PAGE in the buffer system of Laemmli (1970). After electrophoresis, one lane is stained with Coomassie Blue solution to localise the binding protein. The band containing the 170 kDA binding protein is excised from the gel and cut in small pieces. The pieces are then squeezed through a fine metal net to give a suspension ready to be injected It is a further object of the invention to provide an anti-idiotype antibody which reacts specifically with the binding proteins for *B. thuringiensis* δ-endotoxins and their derivatives. A preferred embodiment of the invention relates to an anti-idiotype antibody which reacts specifically with the binding proteins for the *B. thuringiensis* CryIA(b) δ-endotoxin and its derivatives, preferably with the Heliothis binding proteins, most preferably with the *H. virescens* 170 kDa binding protein for the *B. thuringiensis* CryIA(b) δ-endotoxin and its derivatives.

Anti-idiotype antibodies are produced by the immune system of an animal when the antibodies raised against the actual antigen are themselves used as antigen for immunising the animal. The binding region of the anti-idiotype antibody is an image of the binding region of the original antigen.

Particularly preferred within the scope of this invention is an anti-idiotype antibody which reacts specifically with specific regions of the binding protein.

An anti-idiotype antibody of this invention is obtainable by raising antibodies against the native activated toxin and using these antibodies by known methods to produce the anti-idiotype antibodies. The procedure may typically comprise raising antibodies against the native activated toxin and repeatedly immunising with these antibodies. The immunoglobulins directed against the binding proteins for *B. thuringiensis* and its derivatives are thereafter obtained by selection from the serum of the immunised animals, or spleen cells of the immunised animals are fused with corresponding myeloma cells, specific hybridoma cells are selected and the desired anti-idiotype antibody is produced using said hybridoma cells.

Native activated toxins are obtained, for example, by the following procedure: *B. thuringiensis* HD1cryB is transformed with one of the plasmids pXI93, pXI94 and pXI95 according to the method disclosed in EP 342 633 for pXI93 and then cultivated. After cell lysis, residual unlysed cells are disrupted with a cell sonicator and mixtures of spore crystal are harvested. The crystals are dissolved according to the method of Delafield et al. (1968) and activated by a three-hour incubation at 28° C. in a buffer (8 g/l NaCl, 0.2 g/l KCl, 0.05 g/l $NaH_2PO_4·2\ H_2O$, 1 g/l glucose, 1 g/l $NaHCO_3$, 0.68 g/l Na-citrate pH 6.55) which contains 0.05% trypsin and 10 mM triethanolamine pH 10.2. In the case of CryIC toxin, DTT is added to the buffer up to a final concentration of 5 mM. The residual spores or undissolved crystals are removed by centrifugation, 10.000×g, 10 min, 4° C.

Antibodies are raised against the native activated CryIA (b) toxin by performing the above described immunisation strategy using 30 µg of CryLA(b) toxin. Booster injections are administered 4 weeks, 3 months and 4 months later. The injections are made subcutaneously. Blood samples are taken 12 days after an immunisation and then every 2 weeks. The IgGs are separated over a column which contains protein A to which crosslinked agarose is bound, using the eluant 0.1 M acetic acid and 0.15 M NaCl.

An anti-idiotype antibody which reacts specifically with specific regions of the binding proteins for *B. thuringiensis* and its derivatives is obtainable by (a) raising antibodies against the native activated *B. thuringiensis* δ-endotoxin, (b) separating from these antibodies those antibodies which are not directed against specific regions of the toxin by subtractive affinity chromatography, (c) immunising repeatedly with these antibodies which are directed against the specific region of the toxin, and (d1) selecting the immunoglobulins which are directed against specific regions of the binding proteins for *B. thuringiensis* δ-endotoxins and their derivatives, or (d2) fusing spleen cells of the immunised animal with corresponding myeloma cells, selecting specific hybridoma cells and producing the desired anti-idiotype antibodies using said hybridoma cells.

In subtractive affinity chromatography, antibodies which react specifically with a specific toxin and recognise solely determinants of said toxin are separated from such antibodies which cross-react with another toxin or a plurality of other toxins. This is done by passing antibodies against this specific activated toxin over a column which is packed with a matrix to which said toxin is bound. The toxin bound to the matrix binds a mixture of antibodies which are directed against the entire toxin. Some of these antibodies cross-react with other toxins. To separate these antibodies, the antibody mixture is eluted from the column, conveniently with a solution of diethylamine and desoxycholate, and then passed over a second column which is packed with a matrix to which the second toxin is bound or to which a plurality of toxins are bound. The toxin or the mixture of different toxins is chosen such that all antibodies which recognise a specific region of the specific toxin are bound and those antibodies which bind specifically to a specific region of the specific toxin will be found in the flow-through. Crosslinked agarose bound to protein A may typically be used as matrix. Suitable materials are described in the literature.

An essential aspect of the invention resides in the detection of bindings of antibodies to toxins, of toxins to binding proteins and of antibodies to binding proteins, which detection is performed autoradiographically or immunologically by conventional methods familiar to the person skilled in the art (e.g. according to Harlow and Lane, 1988).

The binding of the antibodies to the Cry1A(b) BP of *H. virescens* can be determined conveniently as follows:

(a) BBM proteins are resolved by SDS-PAGE and transferred to a membrane by electrotransfer (0.4 A; 1 h). Unspecific binding is blocked by incubation in TBSTM (10 mM tris, HCl pH 8.0, 150 mM NaCl and 0.5% polyoxyethylene sorbitol monolaurate)+1% non-fat dry milk) (1 h). The membrane is then incubated for at least 2 hours with a suitable dilution of the antibodies in TBSTM. The unbound antibodies are afterwards removed by washing with TBST, followed by further incubation of the membrane with goat-anti-mouse antibodies marked by alkaline phosphatase. Unbound antibodies are removed by washing with TBST. The bound antibodies are visualised by reaction with NBT (p-nitro blue tetrazolium chloride) and BCIP (5-bromo4-4chloro-3-indolylphosphate toluidine salt) in 0.1 M $NaHCO_3$, 1 mM $MgCl_2$, pH 9.8.

(b) BBM proteins are transferred to a membrane with the aid of a so-called slot-blot apparatus (Schleicher and Schull). After saturation in TBSTM, the membrane is incubated with a suitable dilution of the antibodies in TBSTM. After removal of unbound antibodies by washing, the membrane is incubated with a $^{125}$I-labelled antibody directed against this antibody. Then unbound antibodies are removed by washing and the intensity of the autoradiographic signals is measured.

A further object of the invention is the provision of a test kit based on a novel antibody.

A specific embodiment of this invention relates to a test kit which is based on one of the conventionally employed immunoassays, conveniently selected from the group consisting of radioimmunoassay, enzyme-linked immunoassay and chemiluminescence assay. The recipes for such kits depend on the chosen method of detection and are known to the skilled person.

The invention also relates to a method of isolating a novel *B. thuringiensis* δ-endotoxin, which comprises (a) saturating the binding proteins for a given δ-endotoxin by binding antibodies, and (b) binding novel toxins to other binding proteins for pretreated midgut membrane proteins.

The invention also provides another method of isolating a novel *B. thuringiensis* δ-endotoxin by binding to a matrix specific antibodies which are raised against known toxins by subtractive affinity chromatography, and incubating said matrix with the totality of the toxins of a strain or a plurality of strains, such that a novel toxin having other structural features is not recognised by the antibodies and is therefore not bound and remains in the solution. The invention also relates to the resultant novel toxin.

In the context of this invention, the term a "novel" *B. thuringiensis* δ-endotoxin will be understood as meaning a heretofore non-identified or non-identifiable δ-endotoxin.

The invention further provides a method of identifying a novel *B. thuringiensis* δ-endotoxin which recognises a novel binding protein, which comprises saturating the binding proteins of the BBMV of different insects for known δ-endotoxins by binding with said δ-endotoxins and verifying whether the novel toxin does still bind. The invention also relates to the novel toxin which is identifiable by the method described herein.

In yet another of its aspects the invention provides a method of preparing a gene which encodes a novel toxin by deriving the nucleotide sequence wholly or partly from the amino acid sequence, and either synthesising a corresponding gene in accordance with known methods or identifying the naturally occurring gene with the aid of a probe and then isolating said gene. The invention also embraces a method of preparing the gene for a novel toxin by expressing a gene bank of the donor bacterium, verifying the expression products with an antibody against said novel toxin, and isolating from a positive clone the desired gene by conventional methods with which the person skilled in the art is familiar. It will be readily understood that all other known methods of isolating the gene can be applied.

The novel antibodies make it possible to analyse resistance. Thus it is possible to verify whether a specific binding protein is present. Moreover, using a novel anti-idiotype antibody it is possible to determine whether the binding sites of existing binding proteins are changed. Hence the invention relates to the use of a novel antibody for analysing resistance which is attributable to the lack of the binding protein or to the lack of the binding sites, as well as to a method of reducing the resistance development potential in pest control by determining the changes in the number of the binding sites or of the binding proteins and accordingly using a suitable toxin or mixture of toxins.

The invention also has for its object to provide a method of determining the amount of binding protein present with the aid of a novel antibody against said binding protein or of a test kit which contains a novel antibody. The method consists essentially in incubating the sample which contains the binding proteins with the antibodies or the test kit, and subsequently determining the amount of binding protein-antibody complexes.

Using the novel antibodies and the test kits it is possible to determine the degree of relationship between toxin binding proteins by determining the immunological cross-reactivity of the binding proteins. The invention therefore relates to the use of a novel antibody or test kit for analysing the immunological cross-reactivity of toxin-binding proteins to determine their degree of relationship by determining the binding of an antibody against a specific binding protein to immobilised binding proteins of different origin.

The novel antibodies and test kits make it possible to investigate different insects for the availability and accessibility of a binding protein for the corresponding toxin. These antibodies and test kits enable a simple and rapid identification to be made of the binding protein in the gut membrane of target insects. The invention therefore relates to the use of a novel antibody or test kit for determining the availability and accessibility of a binding protein for the corresponding toxin in different insects.

Abbreviations

| | |
|---|---|
| BBM(V) | brush border membrane (vesicle) |
| BCIP | 5-bromo-4-chloro-3-indolylphosphate toluidine salt |
| BP | binding protein |
| BSA | bovine serum albumin |
| CHAPS | 3-[(3-cholamidopropyl)dimethylammonio]-1-propanesulfonate |
| DTT | dithiothreitol |
| EDAC | 1-ethyl-3-(3-dimethylaminopropyl)carbodiimide |
| EGTA | [ethylenebis(oxyethylenenitrilo)]tetraacetic acid |
| ICP | insecticidal crystal protein |
| IgG | immunoglobulin G |
| NBT | p-nitro blue tetrazolium chloride |
| PBS | phosphate buffered saline |
| PMSF | phenylmethylsulfonyl fluoride |
| PVDF | polyvinylidene difluoride |
| SDS-PAGE | sodium dodecylsulfate polyacrylamide gel electrophoresis |
| TBSTM | TBST (10 mM tris-HCl pH 8.0, 150 mM NaCl and 0.5% polyoxyethylene sorbitol monolaurate) + 1% non-fat dry milk |

EXAMPLES

Bacterial strains and plasmid DNA

*B. thuringiensis* HD1cryB has been deposited as *B. thuringiensis* HD1cryβ in accordance with the Budapest Treaty (DSM 4574).

pXI93 has been deposited as pK93 in accordance with the Budapest Treaty (DSM 4571) [contains the cry1A(b) gene from *B. thuringiensis kurstaki* HD1 DSM 3667)].

Deposits

In connection with this invention, the following plasmids have been deposited with the German Collection of Microoganisms in accordance with the Budapest Treaty:

| DSM Number | Date | Plasmid |
|---|---|---|
| DSM 6616 | 23.7.1991 | pXI94 [contains the cryIA(a) gene from B. thuringiensis kurstaki HD1] |
| DSM 6615 | 23.7.1991 | pXI95 [contains the cryIA(c) gene from B. thuringiensis kurstaki HD73] |
| DSM 6614 | 23.7.1991 | pXI109 [contains the cryIC gene from B. thuringiensis GC91 (NCTC 11821)] |

Example 1: CryIA(a), CryLA(b), CryIA(c) and CryIC toxins and their binding to BBM proteins from Heliothis and Spodoptera After SDS-PAGE (total protein 10 µg), the denatured BBM proteins from the midguts of *H. virescens, H. zea, S. littoralis, S. exigua* and *S. litura* larvae are transferred to a PVDF membrane for 1 h at 4° C. 0.4 A (Towbin et al., 1979). The membrane is stained with Ponceau S (0.2% in 3% trichloroacetic acid) (Serva) to visualise total proteins. Nonspecidic binding is blocked by incubation for 30 min at room temperature in TBSTM. The membrane is incubated overnight in 1.5 µg/ml each of activated CryIA(a), CryIA(b), CryIA(c) and CryIC toxins and the unbound toxin is removed by washing in TBST. Bound toxin is identified with the monoclonal antibody 82.1 (Huber-Lukac et al., 1986) or with rabbit antibodies which are directed against CryIC (Example 3) (serum diluted 1:1000 in TBSTM). The unbound antibodies are removed by washing in TBST. Then incubation is carried out for 1 hour at room temperature in goat-anti-mouse or goat-anti-rabbit antibodies marked by alkaline phosphatase. Reaction with NBT and BCIP in 0.1 M $NaHCO_3$ and 1 mM $MgCl_2$, pH 9.8 results in visualisation of the membrane-bound complex.

The three CryIA toxins and the CryIC toxin recognise one or more binding proteins in the midgut of each insect species (Table 1).

TABLE 1

*B. thuringiensis* toxin binding proteins in the midgut of different insects (molecular weights, kDa; SDS-PAGE)

|  | H. zea | H. virescens | S. littoralis | S. exigua | S. litura |
|---|---|---|---|---|---|
| CryIA(a) | 170 | 170 | 160 | 200<br>180 | 150 |
| CryIA(b) | 170 | 170 | 160 | 200<br>180 | 150 |
| CryIA(c) | 150<br>140<br>120 | 140<br>120 | 125<br>115 | 130<br>115 | 125 |
| CryIC | nd | 40 | 40 | 40 | 40 |

In all cases CryIA(a) and CryIA(b) recognise the same proteins, but the binding proteins differ from one insect species to another. CryIA(c) binds to a number of different toxin binding proteins. In case of all three Spodoptera species and *H. virescens* CryIC binds to a binding protein with a molecular weight of 40 kDa.

Example 2: Antibody against the CryIA(b) BP from *H. virescens*

An aliquot of a suspension containing 15 µg of CryLA(b) binding protein from *H. virescens* fixed in gel is injected subcutaneously into the back of a Chinchilla rabbit. Booster injections of 15 µg of protein are administered after 3 and 7 weeks. Serum is collected two weeks after the last booster injection. The serum is separated from whole blood by clotting and low speed centrifugation. The serum is stored in small aliquots at −20° C. until use.

To reduce the background obtained on Western blots when using this antiserum, nonspecific antibodies are removed using an *E. coli* lysate coupled to an affinity column (Sambrook et al., 1989).

Immunological differences between the CryIA(b) BP

The antibodies raised against the CryIA(b) BP from *H. virescens* are used for an immune blotting analysis of BBM proteins of the larvae of five different insect species. This is done by transferring 3 µg of BBM proteins to a membrane using a slot blot apparatus (Schleicher and Schüll). After saturation in TBST milk the membrane is incubated with a suitable dilution of the antibody in TBSTM. After removing the unbound antibodies by washing, the membrane is incubated with $^{125}$I-labelled goat-anti-rabbit antibodies. Then unbound antibodies are removed by washing and the intensity of the autoradiographic signals is measured with a Shimadzu CS-930 TLC Scanner.

The antibodies cross-react only with the binding protein from *H. zea* but not with the proteins of the Spodoptera species. Although the CryLA(b) toxin recognises a binding protein or several binding proteins in each insect, the binding protein from Heliothis is immunologically not identical with the binding proteins from Spodoptera.

Example 3: Antibodies against the CryIC toxin

Antibodies are raised against the activated CryIC toxin by a standard method: 10 µg of activated CryIC toxin in 400 µl of $H_2O$ and an equal volume of Freund's complete adjuvant are injected subcutaneously into the back of a Chinchilla rabbit. Booster injections are administered with the same amount of antigen in Freund's incomplete adjuvant 4 and 10 weeks later. Blood is taken from the animal 12 days after these booster injections and serum is separated IgG's are separated over a column which contains protein A to which crosslinked agarose is bound.

Example 4: Anti-idiotype antibodies

Preparation of anti-idiotype antibodies 40 mg of antibodies against the native activated CryIA(b) toxin are passed over a column packed with aminoalkyl agarose to which 5 mg of CryIA(b) toxin has been crosslinked using EDAC. The column is washed with 50 mM of tris-HCl (pH 8) until no more protein is detectable in the flow-through by absorption at 280 nm. The elution of bound antibodies is effected with a solution of 10 mM of diethylamine and 0.5% of desoxycholate (pH 11.3). The eluted fractions are immediately neutralised by adding ⅕₀th volume of 1 M tris-HCl (pH 8). About 3 mg IgG are eluted and subsequently passed over a column packed with aminoalkyl agarose to which CryIA(c) has been crosslinked. Antibodies recognising the identical region between CryIA (b) and CryIA(c) are able to bind to this column, whereas antibodies which recognise the variable region of CryIA(b) (Geiser et al., 1986) are not and are therefore present in the flow-through. These antibodies (against CryIA(b)) are used to immunise a Chinchilla rabbit (80 µg). Booster injections are administered at 4-week intervals. Blood is taken from the rabbit 12 days after each immunisation and serum is prepared. The different sera are tested for their ability to bind to the 170 kDa *H. virescens* CryIA(b) BP on a Western blot. The anti-idiotype IgGs are purified against the CryIA(b) BP from *H. virescens* by a method of Madara et al. (1990).

Binding of anti-idiotype antibodies to BBM proteins from larvae of five different insect species The anti-idiotype antibodies obtained above are used to investigate whether the toxin attachment site of the binding protein is conserved in the investigated insects. The 170 kDa binding protein from *H. virescens* as well as that from *H. zea* is specifically recognised by the anti-idiotype antibodies. The antibodies do not recognise the BBM binding proteins of the Spodoptera species.

Western blots are carried out using a PVDF membrane according to Towbin et al. (1979). After the transfer of the BBMV proteins to the membrane and blocking the unspecific binding sites with TBSTM, the membranes are incubated with anti-idiotype antibodies (IgG fraction diluted 1:100 in TBSTM). The membrane-bound antibodies are incubated for 1 hour with goat-anti-rabbit antibodies marked by alkaline phosphatase and subsequently visualised by reaction with NBT and BCIP in 0.1 M $NaHCO_3$ and 1 mM $MgCl_2$.

Example 5: Use of antibodies for isolating toxins (a) The parasporal crystals of *B. thuringiensis kurstaki* HD1 are collected as described in Example 1 and proteolytically activated. Then 0.5 mg of the toxin mixture is given to a column packed with crosslinked agarose to which are coupled 5 mg of antibodies on protein A which react specifically with CryIA(a) and CryIA(b). Whereas CryIA(a) and CryIA(b) are bound, a further toxin is present in the flow-through and can be identified by its specific reaction with the toxin attachment proteins in *H. virescens* as CryLA (c).

In like manner, a "novel" toxin can also be isolated If a plurality of "novel" toxins are present in the flow-through, further isolation steps are carried out by known methods, typically by HPLC or 2-D-chromatography, such as SDS-PAGE and isoelectrofocusing.

(b) Native BBMV are transferred by means of a slot blot apparatus (Schleicher and Schüll) to a membrane which is afterwards incubated in TBSTM (Example 2). The binding proteins which react with CryIA(a) are afterwards incubated with this toxin. The toxin CryIA(c) obtained in (a) is labelled with $^{125}I$ and incubated with the charged membrane. The autoradiographic measurement shows that CryIA(c) binds to a binding protein with which CryIA(a) does not react.

This method can also be used for identifying a "novel" δ-endotoxin.

References

Bradford, M. M., Anal. Biochem. 72:248–254 (1976)

Caramori, T., Albertini, A. M., Galizzi, A., Gene 98:37–44 (1991)

Delafield, F. P., Somerville, H. J., Rittenberg, S. C., J. Bacteriol. 96:713–720(1968)

Dixon, B., Biotechnology 9:415 (1991)

Ge, A. Z., Shivarova, N. I., Dean, D. H., Proc. Natl. Acad. Sci. USA 86:4037–4041 (1989)

Geiser, M., Schweitzer, S., Grimm, C., Gene 48:109–118 (1986)

Harlow, Lane, Antibodies—A Laboratory Manual, Cold Spring Harbor Laboratories, Cold Spring Harbor (1988)

Höfte, H., Whiteley, H. R., Microbiol. Rev. 53:242–255 (1989)

Huber-Lukac, M., Jaquet, F., Lüthy, P., Hütter, R., Braun, D. G., Infect. Immun, 54:228–232 (1986)

Laemmli, U.K., Nature 227:680–685 (1970)

Madara, P. J., Banghart, L. R., Jack, L. J. W., Neira, L. M., Mather, I. H., Anal. Biochem. 187:246–250 (1990)

van Rie, J., McGaughey, W. H., Johnson, D. E., Barnett, B. D., van Mellaert, H., Science 247:72–74 (1990)

Sambrook, J., Fritsch, E. F., Maniatis, T., Molecular cloning, a laboratory manual, Cold Spring Harbor Laboratory, Cold Spring Harbor (1989)

Schnepf, H. E., Tomczak, K., Ortega, J. P., Whiteley, H. R., J. Biol. Chem. 265:20923–20930 (1990)

Towbin, H. Staehelin, T., Gordon, J., Proc. Natl. Acad. Sci. U.S.A. 76:4350–4354 (1979)

Wolfersberger, M., Lüthy, P., Maurer, A., Parenti, P., Sacchi, F. V., Giordana, B., Hanozet, G. M., Comp. Biochem. Physiol. 86:301–308 (1987)

EP 292 435

EP 317 511

EP 342 633

EP 400 246

What is claimed is:

1. An antibody which reacts specifically with a *Bacillus thuringiensis* δ-endotoxin binding protein present in brush border membrane vesicles from the midgut of insects.

2. The antibody of claim 1, wherein said binding protein binds CryIA(b) δ-endotoxin.

3. The antibody of claim 2, wherein said binding protein is from Heliothis.

4. The antibody of claim 3, wherein said binding protein is the 170 kDa binding protein from *H. virescens*.

5. A method of determining the amount of binding protein for a *Bacillus thuringiensis* δ-endotoxin present in a brush border membrane sample, said method comprising:
   incubating the brush border membrane sample with the antibody of claim 1; and,
   determining the amount of said binding protein bound to said antibody.

6. A method for determining the degree of relationship of binding proteins for a *Bacillus thuringiensis* δ-endotoxin present in the brush border membrane of the midgut of insects of different origins, said method comprising:
   immobilizing said binding proteins of different origins;
   reacting the antibody of claim 1 with said immobilized binding proteins;
   detecting the complex of said antibody with said immobilized binding proteins whereby the degree of relationship between said toxin-binding proteins is determined.

7. A method for analyzing resistance of an insect to a particular *Bacillus thuringiensis* δ-endotoxin, said method comprising:
   isolating binding proteins for a *Bacillus thuringiensis* δ-endotoxin from the brush border membrane of the midgut of said insect;
   reacting said binding proteins with the antibody of claim 1;
   detecting the presence of binding protein-antibody complexes; and
   determining resistance of said insect.

8. A method for determining the availability of a binding protein for a corresponding toxin in an insect, said method comprising:
   isolating binding proteins for a *Bacillus thuringiensis* δ-endotoxin from the brush border membrane of the midgut of said insect;
   reacting said binding proteins with the antibody of claim 1; and,
   detecting the presence of binding protein-antibody complexes whereby the presence of a protein-antibody complex indicates the availability of a binding protein for a toxin.

9. A test kit containing an antibody which reacts specifically with a *Bacillus thuringiensis* δ-endotoxin binding protein present in brush border membrane vesicles from the midgut of insects and additional immunoassay reagents.

10. A test kit according to claim 9, wherein said binding protein binds CryIA(b) δ-endotoxin.

11. A test kit according to claim 10, wherein said binding protein is from Heliothis.

12. A test kit according to claim 11, wherein said binding protein is the 170 kDa binding protein from *H. virescens*.

13. An antibody which reacts specifically with a *Bacillus thuringiensis* δ-endotoxin binding protein present in a brush border membrane vesicle from the midgut of insects wherein said antibody is obtained by:

preparing a binding protein for a *Bacillus thuringiensis* δ-endotoxin from said brush border membrane vesicle; and, using said binding protein to produce said antibody.

14. The antibody of claim 13, wherein the δ-endotoxins are CryIA(b) δ-endotoxins.

15. The antibody of claim 14, wherein the binding proteins are Heliothis binding proteins.

16. The antibody of claim 15, wherein the binding proteins are *H. virescens* 170 kDa binding proteins.

* * * * *